United States Patent [19]

Leopoldi et al.

[11] Patent Number: 4,743,234
[45] Date of Patent: May 10, 1988

[54] SYRINGE MAGNIFIER

[75] Inventors: Norbert Leopoldi, Chicago; William P. Heinrich, McHenry, both of Ill.

[73] Assignee: The Cloverline, Inc., Chicago, Ill.

[21] Appl. No.: 50,776

[22] Filed: May 18, 1987

[51] Int. Cl.4 .............................................. A61M 5/00
[52] U.S. Cl. ..................................... 604/187; 604/207
[58] Field of Search ................................ 604/187, 207

[56] References Cited

U.S. PATENT DOCUMENTS 2,586,581  2/1952  Tschischeck .................... 604/207 X
3,596,659  8/1971  Glasser ................................. 604/187
4,178,071  12/1979  Asbell ............................ 604/207 X Primary Examiner—John D. Yasko

[57] ABSTRACT

A magnifier for hypodermic syringes, primarily insulin syringes, made from a plastic material, such as acrylic, adapted to fit closely on the cylindrical barrel of a syringe and having an outer rounded surface which is polished and magnifies the numerals and lines on the syringe, with undercut opposing lips on a portion of the magnifier adapted to engage the barrel to removably secure the magnifier on the syringe and having a flat surface on the magnifier for advertising indicia and in at least one form, having a lock-like member engaged over the finger grip member on the syringe to secure the position of the magnifier on the syringe.

5 Claims, 3 Drawing Sheets

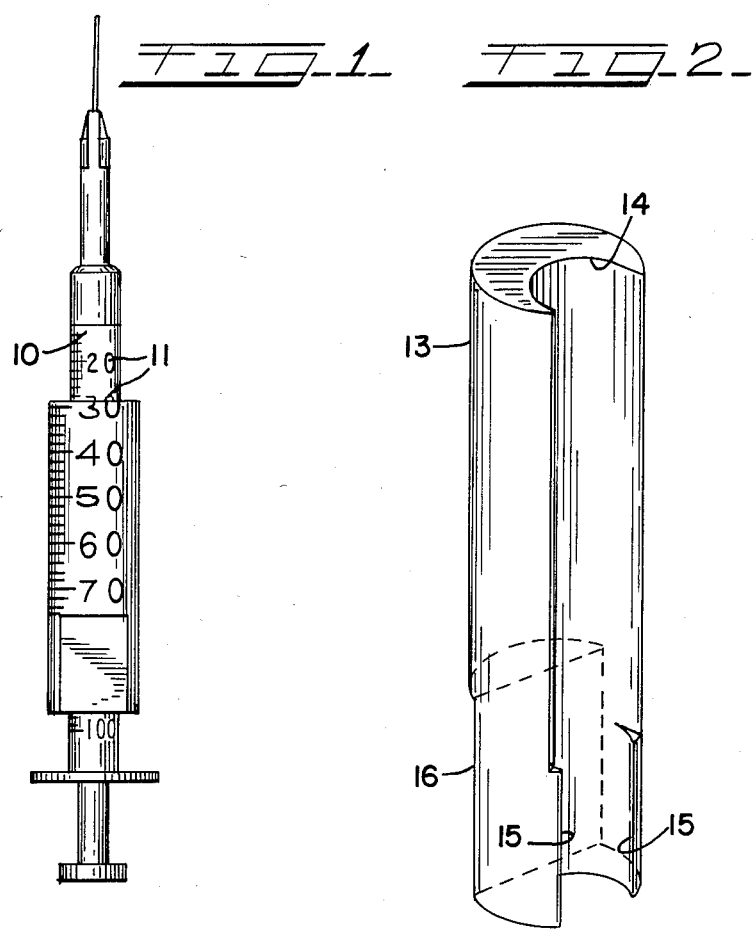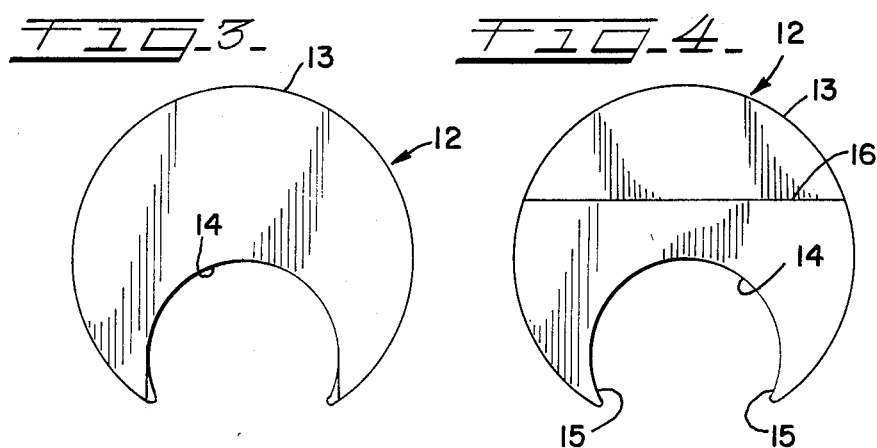

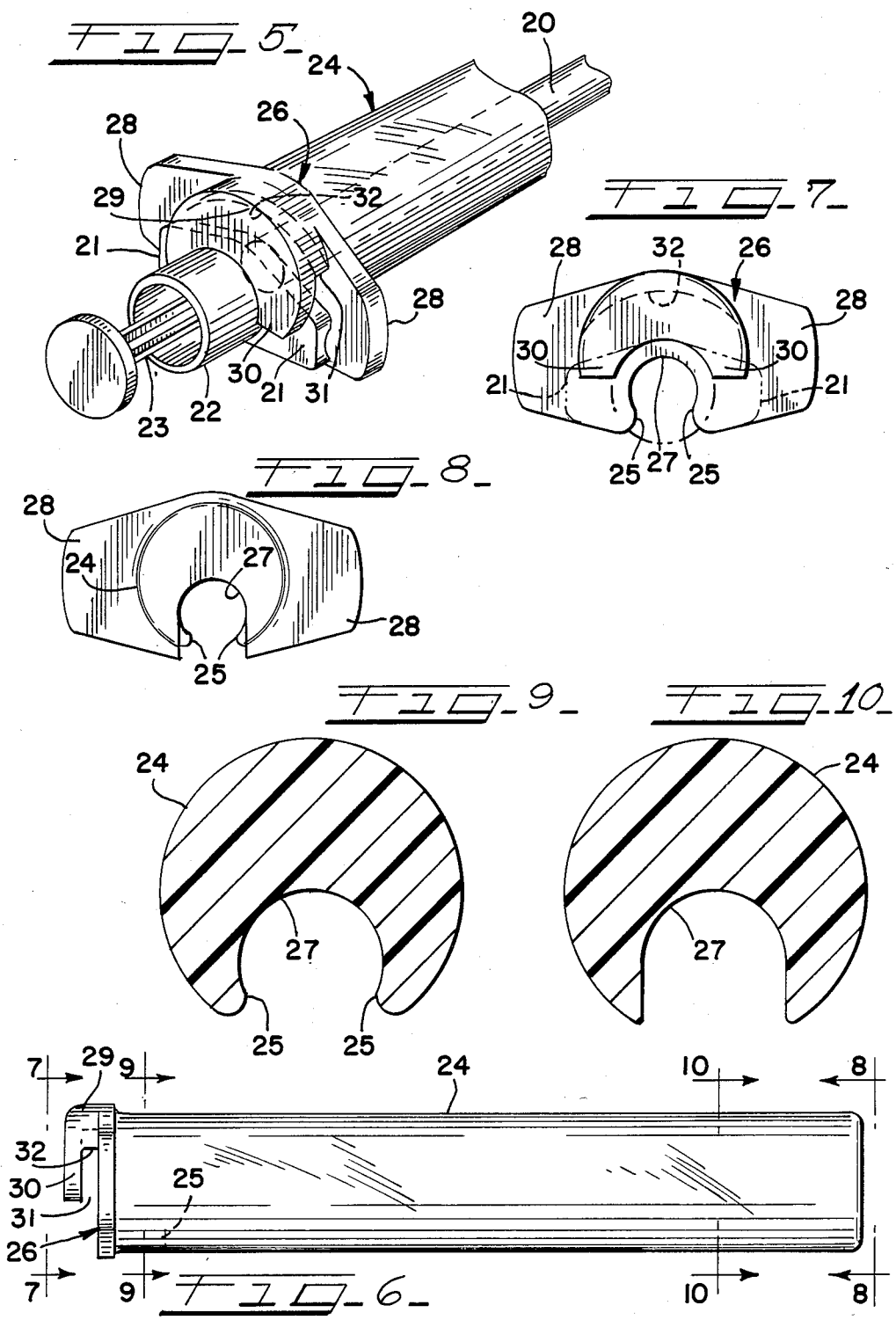

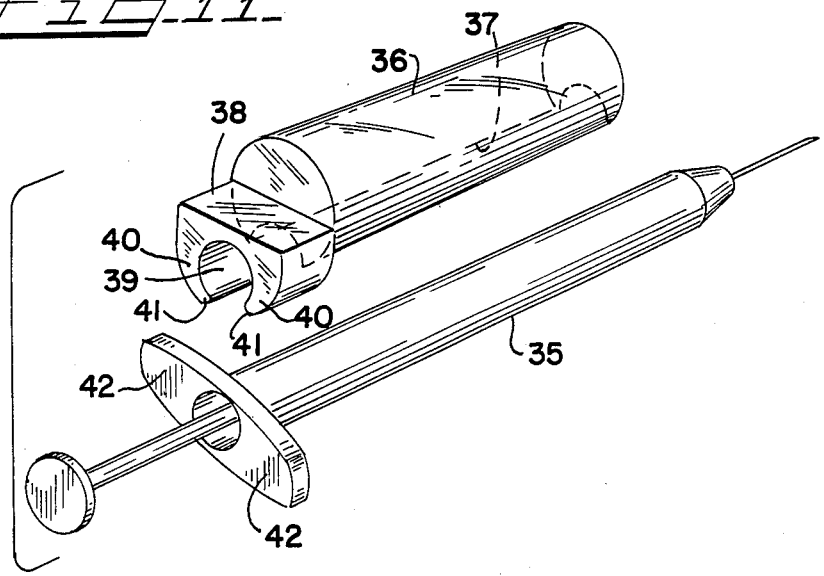
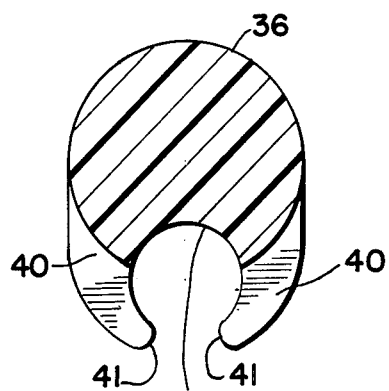

4,743,234

SYRINGE MAGNIFIER

BACKGROUND OF THE INVENTION

Clip-on magnifiers have been available heretofore, but these were adapted to be mounted on the barrel of a syringe by means of metal clips and usually have been the flat type of magnifier that did not fit around the cylindrical surface of the syringe and consequently did not closely engage the syringe barrel so that it was relatively easy to dislodge the attached unit, possibly causing it to be dropped and if made from glass, easily broken.

It is well known that diabetes causes failing eyesight and since diabetics must utilize great care in determining the number of units of insulin to be injected, it is important that they be able to see clearly the graduations on the syringe barrel. However, the flat type of magnifier previously used, did not make for the most easily read graduations on the cylindrical barrel because it projected beyond the sides of the barrel and did not fit around the barrel so that only the central part of the magnifier along the length of the syringe brought the graduations on the barrel into focus. Further, such glass magnifiers were sensitive to temperature, especially high temperatures and it was necessary to exercise care in sterilizing, or cleaning them.

SUMMARY OF THE INVENTION

The present invention provides a clip-on magnifier for a syringe, made from a suitable plastic material, preferably a crystal clear acrylic, and which is molded to fit around the barrel of the syringe to an extent of as much as fifty per cent (50%), with a part of the fit-around portion providing an integral clip adapted securely to hold the magnifier on the syringe while permitting easy removal, when desired. The magnifier is shaped to fit closely around the syringe barrel and throughout the major portion of the length of the fit-around portion is free to slip over the barrel without resistance but, for a relatively short portion of this fit-around length, this portion is provided with a pair of opposed fit-around undercut lips which engage around the syringe barrel and extend beyond the widest diameter of the barrel so that these lips serve to clamp the barrel and hold the magnifier on the syringe, but allowing easy installation and removal of the magnifier relative to the syringe barrel. At the end of the magnifier adapted to be disposed adjacent to the base, or plunger end of the syringe, the magnifier is provided with a locking member which projects beyond this end of the magnifier and is adapted to hook over the finger grips on this end of the syringe barrel to fixedly position the magnifier on the barrel and prevent longitudinal slipping of the magnifier on the barrel. This locking member and the "fit-around undercut lips" are both disposed adjacent to the same end of the magnifier.

The surfaces of the magnifier are highly polished and with the outer surface thereof also being rounded, the graduations on the underlying syringe are magnified and enlarged so that they may easily be read. Being made from plastic the magnifier is generally unbreakable under normal or usual circumstances and is resistant to damage from excess of temperature. The magnifier is proposed to be a "give away" item by doctors prescribing insulin for their patients, or by druggists dispensing syringes and insulin. In this connection, the magnifier is provided with a flat surface facing outwardly which might contain the druggists identity and address, or it might be distributed by a drug supply house whose name would then appear on the indicia portion of the magnifier.

OBJECTS OF THE INVENTION

It is the primary purpose of this invention to provide a magnifier made from clear plastic having rounded contours adapted to fit closely around the cylindrical barrel of a syringe with one or more integral clips engaging beyond the major diameter of the syringe barrel to hold the magnifier on the syringe and in one form having a hook-like locking member adapted to engage over the finger grips on the end of the syringe barrel.

The principal object of the invention is the provision of a one piece, highly polished, clear plastic magnifier adapted to be fitted closely around the barrel of a hypodermic syringe.

An important object of the invention is to provide a clear plastic magnifier having a recess in its underside adapted to fit partially around the curvature of a syringe barrel and having a snap-on clip integrally formed at one end of the magnifier.

An object of the invention is to provide a clear plastic magnifier having a generally semi-cylindrical recess adapted to fit around the barrel of a syringe to the extent of as much as fifty per cent (50%) of the diameter of the barrel.

Another object of the invention is the provision of a clear plastic magnifier with a generally curved recess extending lengthwise thereof to fit on a surface of the cylindrical barrel of a syringe and having opposed undercut lips adjacent to one end of the magnifier which engage the barrel beyond the major diameter thereof.

A further object of the invention is to provide a highly polished plastic magnifier having inner and outer rounded surfaces, adapted to fit closely on the cylindrical barrel of a hypodermic syringe with a flat exterior surface integral with the magnifier containing advertising indicia.

A still further object of the invention is the provision of a generally rounded recess in a clear plastic magnifier to fit on the tubular barrel of a syringe and having a pair of opposed undercut lips at the respectively opposite sides, which engage around the syringe barrel beyond the major diameter thereof adjacent one end of the magnifier and having a locking member projecting beyond this end of the magnifier adapted to engage over the finger grips on the adjacent end of the syringe barrel to fix the position of the magnifier on the syringe.

DESCRIPTION OF THE DRAWINGS

The foregoing and other and more specific objects of the invention are attained by the magnifier illustrated in the accompanying drawings wherein FIG. 1 is a general view of the magnifier shown in its operative form clipped onto the barrel of a hypodermic syringe;

FIG. 2 is a general perspective view of the magnifier showing the rounded magnifying surface, the syringe recess and the undercut lips forming the clip-on feature;

FIG. 3 is an end elevational view from the top, showing the generally cylindrical section of the magnifier and the recess for the syringe;

FIG. 4 also is an end elevational view, but looking from the opposite or bottom end and illustrating the undercut retaining lips and showing the cut-away flat surface for advertising indicia.

FIG. 5 is a general perspective view of a magnifier on a syringe, with portions broken away to enable the arrangement to be shown to larger scale and wherein a locking member is illustrated engaged over the finger grips on the syringe;

FIG. 6 is a full length elevational view of the magnifier shown in FIG. 5 and clearly revealing the hook-like locking member projecting from one end of the magnifier with the fit-around undercut lips indicated in dotted lines at this same end of the magnifier;

FIG. 7 is an end elevational view of the base end of the magnifier with the locking member and the fit-around undercut lips clearly shown;

FIG. 8 also is an end elevational view showing the opposite end of the magnifier;

FIG. 9 is a cross sectional view, taken on the line 9—9 of FIG. 6, showing the section through the magnifier at the position of the fit-around undercut lips adjacent the base end of the magnifier;

FIG. 10 also is a cross sectional view through the magnifier, taken on the line 10—10 of FIG. 6, showing the smooth sided internal recess for closely receiving the barrel of a syringe;

FIG. 11 is an exploded perspective view of a magnifier and syringe where the fastening clip is located at one end of the magnifier and may have advertising indicia on the clip; and FIG. 12 is a cross sectional view through the magnifier.

DESCRIPTION OF GENERAL EMBODIMENT

In FIG. 1 the magnifier is illustrated in its normal use position clipped onto the barrel of a standard hypodermic syringe 10 of the type generally used by diabetics to inject insulin and which contains surface graduations 11 that enable the patient to determine the number of units to be drawn into the syringe for administering the proper dosage. This is of the greatest importance as either an overdose or an underdose can result in more or less severe reactions and must be avoided. The proper reading of the graduations on the syringe is critical also from the standpoint of visibility inasmuch as diabetes affects the eyesight and by magnifying the graduations they can more easily be read even though the eyesight of the patient may be weaker than normal.

The magnifier 12 of this invention, clearly magnifies the size of the surface markings on the syringe barrel, as can readily be seen in FIG. 1 and since the magnifier may easily be clipped onto the syringe it affords the greatest convenience and is always available to assist in reading the graduations. Hypodermic syringes of the type shown in FIG. 1 are usually disposable and are discarded after only one use but since the magnifier is easily applied and removed it may be quickly clipped onto the syringe for use and then just as easily removed for use on another syringe the next time it becomes necessary to inject a proper dose of insulin.

The magnifier 12 comprises a generally cylindrical member molded from crystal clear acrylic and is highly polished on all surfaces so that when looking through the rounded magnifying area the image is clear and undistorted. It will be seen that the rounded surface 13 not only serves to magnify the syringe barrel graduations but enables them to be read not only from straight on but from around the sides of the barrel also and without distortion so that it is not actually absolutely necessary that the magnifier be clipped onto the syringe barrel in direct centered alignment with the graduations on the barrel but might be off center somewhat and the graduations are still clearly readable as the magnifier blends with the graduations.

The magnifier 12 is molded with an integral recess 14 of somewhat semi-cylindrical contour, as best shown in FIGS. 3 and 4, that is so shaped as to closely fit the rounded surface of the syringe 10 whereby the magnifier is maintained in alignment with the barrel of the syringe and the graduations thereon. At the opposite edges of the recess 14 adjacent to one end thereof, a pair of opposing undercut lips 15 are provided for but a portion of the length of the recess and which extend partially around the barrel of the syringe 10 beyond the point of maximum diameter of the barrel so that the opposing lips 15 function like spring clips to engage the barrel and retain the magnifier on the syringe. The material of the magnifier is such and the plastic syringe is sufficiently elastic to permit of the clips 15 adjusting sufficiently with the flexing, or slight compression of the barrel, for the clips to pass over the maximum diameter of the barrel 10 and then the barrel springs back into full rounded engagement with the magnifier and the barrel beyond that point where the clips are engaged is closely engaged in the recess 14 to securely hold the magnifier and the syringe in proper relation while the graduations are being read.

The magnifier 12 is provided with a cut-away flat surface 16 adjacent to one end thereof and which may be utilized for advertising indicia by the supplier of the magnifying unit. The magnifier is intended to be furnished as a give-away item to be supplied by the manufacturer of the unit, or by a druggist, or a drug supplier, or by a doctor. If supplied by the doctor it would be given to the patient at the time of prescribing insulin and if furnished by the druggist it would be given to the patient at the time of filling the prescription for the insulin and/or the syringes. In any event the surface 16 would be utilized to incorporate the name and address of the party furnishing the magnifier.

The advertising surface 16 is shown as being provided on the face of the magnifier adjacent to one end thereof but this could be provided in the form of a lengthwise extending flat surface on one side of the unit, or it might be provided on both sides of the magnifier with the graduation viewing magnifying surface 13 disposed between the two flat surfaces without seriously affecting the viewing area of the magnifier and whereby the magnifying area might extend full length of the magnifier. Further, the retaining clips 15 are disclosed as being provided only at one end of the magnifier but similar undercut clips of lesser extent might be provided at respectively opposite ends of the recess 14 without seriously affecting the ready application and removal of the magnifier in relation to a syringe.

The magnifier affords the further important advantage of enabling the user more readily to observe whether any bubbles may be in the syringe and thus expel them before the dosage is injected under the skin since it is important that any air in the syringe be eliminated before the injection is made.

DESCRIPTION OF SECOND EMBODIMENT

The invention, as shown in FIGS. 5 through 10, includes an advanced feature which makes this design a desirable form of the invention. The magnifier is shown fully in FIG. 6 but fragmentary FIG. 5 best illustrates that the lips 25 are disposed respectively at opposite sides of the lengthwise recess 27 so that when the syringe barrel 20 is disposed in the recess the lips 25 will extend around and more or less underlie the major diameter of the syringe. The syringe being made from a suitable plastic material is somewhat flexible and will deflect, or compress to some extent when the opposed lips 25 are pressed into position over the barrel 20 and of course will spring back when the magnifier has reached its final position with the barrel 20 in the recess 27 and the opposite lips 25 embracing the syringe. In this respect the magnifier 24 is adapted to function similarly to the magnifier 13.

At the base end 26 of the magnifier it is provided with finger grips 28 projecting out from the respectively opposite sides of the syringe and when the magnifier is installed in position on the syringe these grips are disposed in a position adjoining and immediately backing up the finger grips 21 on the syringe. These finger grips 28 are of greater extent than the grips 21 on the syringe and in the use of the syringe, may be utilized in holding the syringe while actuating the plunger 23 to force the contents out of the barrel 20 through a needle (not shown). In this operation, the finger grips 28 function just as though they were a part of the syringe since they are disposed in contact with the finger grips 21 and of course are backed up by the smaller finger grips when the plunger 23 is squeezed between a thumb and the fingers engaging the grips 28 on the side opposite from the grips 21. This is especially true when the magnifier may require some degree of rotation around the syringe to align the graduations on the syringe with the best viewing angle through the magnifier.

The graduations on the syringe barrel 20 are applied by means of automatic printing machines and these machines are not capable of printing the graduations on the barrel in the same position every time. Consequently, the markings may be in any position around the barrel irrespective of their relationship to the positions of the finger grips 21 so that on one syringe they may be centered on what may be called the top of the syringe barrel with the finger grips extending to the opposite sides while on another syringe they may be printed on the side of the barrel in one of the areas where the finger grips project laterally. For this reason the syringe barrel 20 must be freeely rotatable relative to the magnifiers.

An important feature of this magnifier installation on the syringe is the provision for locking the magnifier on the syringe and to prevent relative axial movement of the magnifier on the barrel 20. A locking member 29 is integral with the finger grips 28 on the magnifier and projects outwardly therefrom to overlie the finger grips 21 on the syringe, as best shown in FIG. 5. The locking member extends downwardly over the finger grips 21 at each side of the collar barrel 22, as at 30. The locking member is provided with an upward recess 31 into which the finger grip elements 21 are received and the surface 32 of this recess overlying the finger grips 21 is constructed on a curvature the arc of which is adapted to accommodate the swinging of the outstanding finger grips 21 when the syringe barrel 20 is rotated in the magnifier 24 when it is necessary to line up the best viewing position thereof with the graduations printed on the barrel.

DESCRIPTION OF THIRD EMBODIMENT

In FIG. 11 another form of the clip-on magnifier is illustrated in spaced relation to a syringe with the magnifier in position to be brought into engagement with the barrel of the syringe where the end clip can be snapped over the barrel to hold the magnifier on the syringe. In this form of the invention a typical insulin syringe 35 is disclosed as being of the type now being marketed as a monoject, or Plastipak, an important characteristic of which, that makes these syringes popular with diabetics, is their slim size and small, very sharp needles which make them more comfortable to use. The syringe is plastic and therefore flexible to some extent.

The magnifier 36 for this type syringe is molded from a clear acrylic material and highly polished like the previous forms of the invention. The magnifier 36 is of a length such as to extend substantially the major length ef the syringe 35 whereby the indicia on the syringe barrel can be magnified for easy reading over the approximate full length of the barrel. The magnifier is rounded and provided with a rounded recess 37 on its bottom side where it engages the syringe barrel. However, this recess is relatively shallow and is not semi-cylindrical as in the previous forms, so that it will not extend over, or around, the major diameter of the syringe barrel, nor will it enclose, or confine, the syringe within the recess but fits over but a small portion of the curved surface of the barrel whereby the great bulk, or cross section, of the magnifier is disposed above the syringe barrel, preferably directly over the figures to be read on such top surface. In this manner the magnifier may be utilized to increase the magnification power thereof, as desired.

At one end of the magnifier beyond the magnifying area, a clip-on bracket 38 is formed integrally with the body of the magnifier and has an end opening 39, the upper portion of which is aligned with the recess 37. The bracket 38 is generally flat on top and this surface may be utilized to incorporate a brief advertising message, or a name, if preferred. The bracket is adapted to encircle the barrel of the syringe for more than half of its section whereby it extends beyond the major diameter of the syringe barrel and for this purpose the side walls 40 of the bracket extend downwardly and wrap around the barrel and terminate in inwardly directed lips 41 which engage under the barrel to form a secure, if non-permanent, attachment to the barrel. The acrylic material of the magnifier is relatively hard but the syringe 36 being flexible, will deflect to enable the bracket 38 to be engaged therearound and then will spring back to its normally round shape withing the confines of the bracket opening 39. The syringe, of course, is the throw away type to be discarded after one use, but the magnifier can be removed readily enough and used again on another syringe. The magnifier 37 is designed for application to the syringe 35 with the clip-on bracket 38 disposed immediately behind the finger grips 42 on the syringe barrel.

From the foregoing it will be seen that a magnifier has been provided which may easily be installed on the barrel of a hypodermic syringe to render the graduations on the syringe more easily readable and air bubbles more readily visible for expulsion and which is made from a highly polished crystal clear acrylic in the form of an integral one piece unit adapted to be clipped onto the syringe barrel over the graduations with the syringe closely fitting into a recess in the magnifier for alignment therewith and having flexible retaining clips retaining the unit on the syringe which are integral parts of the unit and a locking device adapted to engage over the finger grips on the syringe to fix the relative position of the magnifier on the syringe barrel, but permitting rotation of the syringe within the magnifier, including the syringe finger grips.

What is claimed is:

1. A syringe magnifier made from a crystal clear plastic material comprising a generally elongated solid member having a generally rounded outer magnifying surface, a generally rounded inner surface forming a recess extending lengthwise of the member, and an integral retaining clip having an undercut lip extending along an edge of said recess, and a complementally opposed updercut lip extending along an opposite edge of said recess.

2. A syringe magnifier as set forth in claim 1 wherein said recess is of relatively shallow depth extending less than half of the diameter of a syringe on which the magnifier is mounted.

3. A syringe magnifier as in claim 1 wherein said undercut lips extend for only a portio of the total length of said recess.

4. A syringe magnifier as in claim 2 wherein said integral retaining clip is located at one end of the magnifier beyond the magnifying area.

5. A syringe magnifier as in claim 4 wherein said retaining clip has a flat top surface and depending side walls terminating in inwardly directed lips.

* * * * *